United States Patent [19]
Smit et al.

[11] Patent Number: 5,473,090
[45] Date of Patent: Dec. 5, 1995

[54] PROCESS FOR THE PREPARATION OF TRIALKYL COMPOUNDS OF GROUP 3A METALS

[75] Inventors: Cornellis J. Smit, Heemskerk; Aart J. Van Der Lee, Barneveld; Gerbrand J. M. Van Eijden, Utrecht, all of Netherlands

[73] Assignee: Air Products and Chemicals, Inc., Allentown, Pa.

[21] Appl. No.: 360,845

[22] PCT Filed: Jul. 2, 1992

[86] PCT No.: PCT/EP93/01770

§ 371 Date: Feb. 27, 1995

§ 102(e) Date: Feb. 27, 1995

[87] PCT Pub. No.: WO94/01438

PCT Pub. Date: Jan. 20, 1994

[30] Foreign Application Priority Data

Jul. 2, 1992 [GB] United Kingdom ................. 92202017

[51] Int. Cl.$^6$ ................. C07F 5/00; C07F 5/02; C07F 5/06
[52] U.S. Cl. ................. 556/1; 568/7; 427/585; 427/586; 427/593
[58] Field of Search ................. 556/1, 89; 568/7; 427/585, 586, 593

[56] References Cited

U.S. PATENT DOCUMENTS 2,863,894  12/1958  Smith ..................................... 260/448

FOREIGN PATENT DOCUMENTS

| 0372138 | 6/1990 | European Pat. Off. . |
| 1310128 | 11/1961 | France . |
| 2123423 | 6/1983 | United Kingdom . |
| 2183651 | 11/1986 | United Kingdom . |
| 8504405 | 10/1985 | WIPO . |

OTHER PUBLICATIONS

Purification of Group III Metal Alkyls Using Nitrogen Donor Ligands., Foster, et al. *Chemtronics*, 1988, vol. 3, Mar., pp. 38–43.
*Chemical Abstracts*, vol. 11, 1990, p. 728.

*Primary Examiner*—Porfirio Nazario-Gonzales
*Attorney, Agent, or Firm*—Geoffrey L. Chase; William F. Marsh

[57] ABSTRACT

Process for the preparation of trialkyl compound of a Group 3a metal, in which a Group 3a metal is contacted with an alkyl halide in the presence of an alkali metal to obtain a trialkyl compound of the Group 3a metal and alkali-metal halide.

12 Claims, No Drawings

PROCESS FOR THE PREPARATION OF TRIALKYL COMPOUNDS OF GROUP 3A METALS

This application is a request for U.S. examination under 35 U.S.C. 371 of International application No. PCT/EP93/01770, filed on Jul. 1, 1993.

The present invention relates to the preparation of trialkyl compounds of Group 3a metals. These organometallic compounds find increasing use in the semiconductor industry. In this industry a Group 3a metal compound is deposited onto suitable substrates, generally together with one or more compounds of a Group 5 element, such as arsenic or phosphorus. The deposition of such compounds can be carried out via the decomposition of organometallic compounds from the vapor phase. Such decomposition is known as Metal Organic Chemical Vapor Deposition (MOCVD). When epitaxial layers are grown from such decomposition the technique is better known as Metal Organic Vapor Phase Epitaxy (MOVPE).

A convenient route for the preparation of such trialkyl compounds is via the reaction of Group 3a metal chlorides with either a Grignard reagent, viz. an alkylmagnesium halide, or an alkyllithium compound. A disadvantage of these methods resides in the use of the Group 3a metal chlorides, which are difficult to obtain in the high purity that is required for further use in the semiconductor industry. High purity metals are available commercially and represent therefore a suitable starting material for the preparation of trialkyl compounds of such Group 3a metals.

In the preparation of alkyl compounds of Group 3a metal frequent use is made of elemental Group 3a metal in combination with magnesium.

In Japanese application No. 01/301,684 the preparation of alkyl gallium and alkyl indium compounds is described using a gallium-magnesium or an indium-magnesium alloy, respectively.

In UK patent specification No. 2,123,423 a process for the preparation of trimethylgallium or triethylgallium is described in which an alloy $Ga_2Mg_5$ is reacted with methyl iodide in the presence of an ether. The ether may be a relatively volatile ether, such as diethyl ether, or an ether with a relatively high boiling point, e.g. di-isopentyl ether or diphenyl ether.

The use of magnesium has the drawback that commercially pure magnesium still contains minor amounts of zinc and silicon. Because unintentional zinc and silicon doping in the MOCVD or MOVPE of trialkyl compounds of Group 3a metals needs to be avoided, it would be desirable if different metals or alloys could be used in combination with Group 3a elements.

Accordingly, the present invention provides a process for the preparation of trialkyl compounds of Group 3a metals, in which a Group 3a metal is contacted with an alkyl halide in the presence of an alkali metal to obtain the trialkyl compound of the Group 3a metal and alkali-metal halide.

The advantage of the invention vis-à-vis the above processes is the use of alkali metal which in commercially pure form does not contain zinc in detectable amounts.

The halogen moiety of the alkyl halide can be selected from chlorine, bromine, iodine or mixtures thereof. Especially alkyl bromides and/or alkyl iodides are advantageously used in the present process.

The alkyl groups in the trialkyl compounds may be normal or branched. Although the present process can be carried out with a wide variety of alkyl halides, including those having long chain alkyl groups, the use of alkyl groups with more than 6 carbon atoms is not practical, since the trialkyl Group 3a metal compounds thus obtained have a decreasing thermal stability. Therefore, the alkyl group in the alkyl halide has preferably from 1 to 5 carbon atoms. More preferably, the alkyl moieties are methyl or ethyl groups or mixtures thereof.

The reaction may be carried out under very mild conditions. The pressure may be atmospheric, but also subatmospheric or superatmospheric pressures are feasible. Generally, the pressure is from 0.1 to 10 bar. Since it is most convenient to operate at atmospheric pressure the process is preferably carried out at such pressure. The trialkyl compound is prepared under an inert atmosphere, e.g. under nitrogen, argon or helium. The reaction temperature may vary between wide ranges but will be below the decomposition temperature of the desired compound. For convenience sake the temperature is suitably from ambient to about 200° C. Preferably, the process is carried out at a temperature from 50° to 160° C. Since the reaction is exothermic, it is advantageous if the process is carried out in the presence of a solvent. Not only will the solvent ensure a homogeneous distribution of the reactants, but it also provides a convenient means for controlling the transfer of the heat evolved. A wide variety of solvents may be used in the present process. Such solvents include aliphatic or aromatic hydrocarbons, such as pentane, hexane, heptane, benzene, toluene or xylene. Preferably the solvents contain at least one moiety with electron-donating properties. Examples of such moieties are nitrogen and oxygen atoms. Therefore, suitably amides, such as dimethyl formamide, and, more preferably, ethers are used as solvents. The ethers may be cyclic or non-cyclic. They preferably contain from 3 to 18 carbon atoms. Suitable ethers include dioxane or tetrahydrofuran and diethyl ether, diphenyl ether, di-(iso-)propyl ether, di-isopentyl ether and mixtures thereof.

The Group 3a metals that can be used in the process of the present invention include aluminum, gallium and indium. Preferably indium is used. In the case of indium the reaction is preferably carried out in a hydrocarbon solvent. The reaction runs smoothly and pure trialkyl indium is formed. This represents an advantage over the use of an ether solvent, because the latter use results in the formation of trialkyl indium-ether adducts. It will be clear that such adducts require further purification.

The alkyl halide is preferably used in an amount sufficient to convert all the Group 3a metal. On the other hand, use of a large excess of the alkyl halide is generally avoided since this excess would only add to the costs and hinder easy recovery of the desired product. Therefore, the amount of alkyl halide suitably ranges from 3.0 to 5.0, preferably from 3.0 to 3.5 mole per gramatom Group 3a metal. Preferably the molar amount of alkyl halide is substantially equal to that of alkali metal in gramatom. This ensures a good conversion of the metals into the trialkyl compounds and alkali metal halide.

The processes according to the above Japanese and UK references employ an alloy with an atomic ratio of the Group 3a metal to magnesium of 2–10. In the present process it is possible to use the alkali metal in a substoichiometric amount, e.g. in an atomic ratio of 1:1. Higher atomic ratios are preferred. Therefore, the amount of alkali metal preferably ranges from 2.5 to 6.0 moles alkali metal per mole Group 3a metal. It is advantageous to use a substantially stoichiometric amount of alkali metal compared to the Group 3a metal used (i.e. 3.0 moles of alkali metal per mole Group 3a metal).

Surprisingly, it has been found that the purity of the product obtained is further enhanced if a relatively small excess of alkali metal is employed. Therefore, the atomic ratio of alkali metal to Group 3a metal is more preferably from 3.0 to 3.5. The form in which the Group 3a metal and alkali metal are present in the reaction mixture is not critical. It is possible to use a physical mixture of the alkali metal and the Group 3a metal involved. It is also feasible to employ an alloy of the metals. The relative amounts in the alloy or the mixture are suitably selected such that they correspond with the above molar ratios.

As alkali metal, lithium, sodium, potassium and cesium may be used. The use of lithium is preferred because it is easy to handle, is available in relatively pure form, and gives the highest yields in the process of the invention.

After completion of the reaction, the reaction mixture will contain the trialkyl compound, alkali metal halide and, possibly, some alkali-metal alkyl. The trialkyl compound therefore needs to be separated from the alkali-metal halide. All conventional techniques may be applied to obtain such separation. These techniques include filtration, decantation etc. Conveniently, the trialkyl compound is recovered by distillation. After a first distillation a second fractional distillation may be applied. In the isolation of the trialkyl compound from the reaction mixture by distillation it may be advantageous to recover the first 1 to 10 percent by volume of the product separately. In such a case the main fraction which is then recovered as the desired product has an enhanced purity. The first fraction of the distilled product may be recycled to the original reaction mixture, be used in a subsequent batch of the same reaction, or be discarded. In order to avoid any possible thermal decomposition of the trialkyl compound, the distillation may be carried out under subatmospheric pressure, thereby lowering the boiling point of the trialkyl compounds. The value of the distillation pressure depends to a large extent on the number of carbon atoms in the alkyl groups because such numbers influence the decomposition temperature and boiling point of the trialkyl compound. For distillation of trimethylgallium the pressure can be atmospheric. For trialkyl compounds with higher alkyl groups the decomposition temperature may be lower than the atmospheric distillation temperature and therefore the distillation pressure is preferably lower than 1 bar. In view hereof, the distillation pressures can suitably be selected up to 1000 mbar, and is preferably from <1 to 500 mbar.

The invention is further illustrated by means of the following examples.

EXAMPLE 1

SYNTHESIS OF TRIMETHYLGALLIUM (TMG)

1.1. Use of a GaLi$_3$ alloy

A stoichiometric quantity of lithium (22.8 g) was added to a gallium melt (76.5 g) to form a GaLi$_3$ alloy in an alumina crucible in a glove box under an atmosphere of purified argon. The crucible was placed in a resistance furnace and after stirring at a temperature of 600° C. the melt was allowed to cool. The obtained alloy was crushed and milled in a tungsten carbide mill to a particle size of 0.5–1.0 mm. A 250 ml three-necked round-bottomed flask was charged with 75.25 g (0.83 moles) of GaLi$_3$ and 109 g of freshly distilled di-isopentyl ether. Methyl iodide (354 g) was gradually added such that the temperature did not exceed 125° C. The reaction mixture was stirred for 60 hours at a temperature of 55° C., giving a grey/white suspension. After the reaction the crude TMG was collected by fractional distillation. The yield of TMG was 25 g (26%, based on gallium). Analysis of the crude product by ICP-OES showed it to contain 0.08 mg/kg of silicon as the main impurity.

1.2. Use of a mixture of gallium and lithium

A 500 ml three-necked round-bottomed flask was charged with 15.95 g (2.3 moles) of lithium powder and 49.02 g (0.7 moles) of gallium and 250 g of freshly distilled di-isopentyl ether. Methyl iodide was added at such a rate that the temperature did not exceed 165° C. The reaction mixture was allowed to reflux overnight at a temperature of 135° C. Fractional distillation of the reaction mixture afforded trimethylgallium in 13% yield (relative to gallium).

EXAMPLE 2

SYNTHESIS OF TRIMETHYLINDIUM AND TRIETHYLINDIUM

In all experiments lithium powder (325 mesh) and indium beads (1 mm) were weighed into a three-necked round-bottomed flask in a glove box under an atmosphere of purified argon. The closed three-necked round-bottom flask was subsequently evacuated and back filled with purified argon several times. Solvent was added with a syringe through a septum. Subsequently, the alkyl halide was added through the septum using a syringe. The reaction mixtures were refluxed overnight and subsequently filtered into another three-necked flask. Subsequently, the solvent was evaporated and the final product was isolated via trap to trap distillation. The reaction mixtures and the isolated products were analyzed by both $^1$H-NMR and $^{13}$C-NMR. The yield of the obtained products was determined from the NMR spectra in combination with the weight of the indium that could be recovered unchanged after the reaction. The yields are based on the amount of indium originally present. The nature and amount of the reagents and the results of the reactions are shown in the following Table.

TABLE

| Experiment No. | Li mole | In mole | Solvent | Amount ml | Alkyl iodide | Amount mole | Yield % |
| --- | --- | --- | --- | --- | --- | --- | --- |
| 1 | 0.031 | 0.01 | diethyl ether | 15 | methyl | 0.032 | 96[a] |
| 2 | 0.05 | 0.0167 | n-hexane | 20 | methyl | 0.05 | 84 |
| 3 | 0.025 | 0.008 | diethyl ether | 20 | ethyl | 0.025 | 46[a] |
| 4 | 0.024 | 0.008 | n-hexane | 15 | ethyl | 0.024 | 30 |

[a]The adduct of trialkyl indium with diethyl ether was obtained.

COMPARATIVE EXAMPLE

To show the surprising nature of the smooth reaction of indium and alkali metal in a hydrocarbon solvent, the following experiment was carried out.

Magnesium (0.41 g, 0.016 moles) and indium (1.30 g, 0.011 moles) were added together in a glove box under an atmosphere of purified argon. Via a syringe 25 ml of n-hexane was added, followed by the careful addition of (4.80 g, 0.034 moles) of methyl iodide. After addition of methyl iodide the mixture was allowed to reflux overnight. Subsequently, the reaction mixture was filtered and a NMR spectrum of the resulting clear solution was made. No trace of trimethyl indium could be determined in the mixture. In addition, almost all of the indium (99.2 %) could be recovered after the reaction.

We claim:

1. Process for the preparation of trialkyl compounds of Group 3a metals, in which a Group 3a metal is contacted with an alkyl halide in the presence of an alkali metal to obtain a trialkyl compound of the Group 3a metal and alkali-metal halide.

2. Process according to claim 1, in which the atomic ratio of alkali metal to Group 3a metal ranges from 2.5:1 to 6:1.

3. Process according to claim 1, in which the Group 3a metal is indium.

4. Process according to claim 1, in which the alkali metal is lithium.

5. Process according to claim 1, in which the alkyl halide comprises an alkyl bromide, alkyl iodide or mixtures thereof.

6. Process according to claim 1, in which the alkyl halide has an alkyl moiety with 1–5 carbon atoms.

7. Process according to claim 6, in which the alkyl moiety is a methyl or ethyl group.

8. Process according to claim 1, which is carried out in the presence of a solvent.

9. Process according to claim 8, in which the solvent is an ether.

10. Process according to claim 9, in which the ether is diethyl ether, di-(iso)propyl ether, di-isopentyl ether, diphenyl ether or mixtures thereof.

11. Process according to claim 3, which is carried out in the presence of a hydrocarbon solvent.

12. Process according to claim 11, in which the hydrocarbon solvent is one or more selected from the group consisting of pentane, hexane, heptane, benzene, toluene and xylene.

* * * * *